(12) United States Patent
Angell et al.

(10) Patent No.: US 8,041,516 B2
(45) Date of Patent: Oct. 18, 2011

(54) IDENTIFYING AND GENERATING OLFACTORY COHORTS BASED ON OLFACTORY SENSOR INPUT

(75) Inventors: Robert Lee Angell, Salt Lake City, UT (US); Robert R Friedlander, Southbury, CT (US); James R Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 451 days.

(21) Appl. No.: 12/277,122

(22) Filed: Nov. 24, 2008

(65) Prior Publication Data

US 2010/0131206 A1 May 27, 2010

(51) Int. Cl.
*G06F 19/00* (2011.01)
(52) U.S. Cl. ......................................................... 702/23
(58) Field of Classification Search .................... 702/23, 702/24, 182–185, 188
See application file for complete search history.

(56) References Cited

U.S. PATENT DOCUMENTS

| | | | |
|---|---|---|---|
| 6,242,186 B1 | 6/2001 | Salonen | |
| 7,538,658 B2 | 5/2009 | Twitchell | |
| 2004/0225202 A1 | 11/2004 | Skinner | |
| 2005/0125325 A1 | 6/2005 | Chai et al. | |
| 2006/0000420 A1 | 1/2006 | Davies | |
| 2008/0055049 A1 | 3/2008 | Weill et al. | |
| 2008/0262743 A1* | 10/2008 | Lewis et al. | 702/19 |
| 2009/0070138 A1 | 3/2009 | Langheier et al. | |
| 2010/0131263 A1 | 5/2010 | Angell et al. | |
| 2010/0148970 A1 | 6/2010 | Angell et al. | |
| 2010/0153146 A1 | 6/2010 | Angell et al. | |
| 2010/0153147 A1 | 6/2010 | Angell et al. | |
| 2010/0153180 A1 | 6/2010 | Angell et al. | |
| 2010/0153353 A1 | 6/2010 | Angell et al. | |
| 2010/0153390 A1 | 6/2010 | Angell et al. | |
| 2010/0153398 A1 | 6/2010 | Miller et al. | |

OTHER PUBLICATIONS

U.S. Appl. No. 12/333,323, filed Dec. 12, 2008, Angell et al.
U.S. Appl. No. 12/333,256, filed Dec. 11, 2008, Angell et al.
U.S. Appl. No. 12/333,321, filed Dec. 12, 2008, Angell et al.
U.S. Appl. No. 12/333,323, filed Dec. 15, 2008, Angell et al.
U.S. Appl. No. 12/335,731, filed Dec. 16, 2008, Angell et al.
U.S. Appl. No. 12/336,440, filed Dec. 16, 2008, Angell et al.
U.S. Appl. No. 12/336,471, filed Dec. 16, 2008, Angell et al.
U.S. Appl. No. 12/336,488, filed Dec. 16, 2008, Angell et al.
Brown et al., "IBM Smart Surveillance System (S3): An Open and Extendible Architecture for Smart Video Surveillance", Retrieved on Jan. 12, 2009, pp. 1-4.
U.S. Appl. No. 12/333,311: Non-Final Office Action Mailed Feb. 28, 2011.
U.S. Appl. No. 12/333,321: Non-Final Office Action Mailed May 23, 2011.
U.S. Appl. No. 12/333,256: Non-Final Office Action Mailed May 23, 2011.

* cited by examiner

*Primary Examiner* — Edward Raymond
(74) *Attorney, Agent, or Firm* — John R. Pivnichny; Law Office of Jim Boice (57) ABSTRACT

A computer implemented method, apparatus, and computer program product for generating olfactory cohorts. Olfactory data is received from a set of chemical sensors. The olfactory data describes a set of olfactory patterns for an air sample. The olfactory data is processed to identify attributes of particles in the air sample and generate digital olfactory data. The digital olfactory data comprises metadata describing the attributes of the particles in the air sample to form digital olfactory data. A set of olfactory cohorts is generated using the attributes in the digital olfactory data.

20 Claims, 4 Drawing Sheets

IDENTIFYING AND GENERATING OLFACTORY COHORTS BASED ON OLFACTORY SENSOR INPUT

BACKGROUND OF THE INVENTION

1. Field of the Invention

The present invention relates generally to an improved data processing system and in particular to a method and apparatus for generating cohorts. More particularly, the present invention is directed to a computer implemented method, apparatus, and computer usable program code for processing olfactory sensory input to generate olfactory cohorts.

2. Description of the Related Art

It is sometimes useful to be able to distinguish different aromas and identify sources of particular aromas. For example, it may be important to distinguish the smell of a particular gas and the origin of the smell to identify a location of a gas leak in a pipe. Aroma identification may be performed by a human using the human sense of smell and personal experience to identify different scents. In addition, dogs, which typically have a more sensitive sense of smell, may sometimes be trained to identify a particular source of an aroma far more effectively than a human. For example, cadaver dogs may be used to locate bodies in a disaster area, drug sniffing dogs can be trained to react to the scent of certain illegal drugs, and some dogs have even been trained to smell cancer. However, these methods are limited by the natural limitations of human and animal senses and ability to distinguish a particular scent from the multitude of aromas in the environment.

Currently, electronic sensing technologies are being used to artificially reproduce the sense of smell. An electronic nose is an example of an electronic sensing device that detects aromas by using an array of sensors that are capable of conducting electricity. When the sensors are exposed to a particular aroma, the electricity conducting capabilities of the sensors are altered in a "pattern" that may be used to distinguish and identify different aromas.

BRIEF SUMMARY OF THE INVENTION

According to one embodiment of the present invention, a computer implemented method, apparatus, and computer program product for generating olfactory cohorts is provided. Olfactory data is received from a set of chemical sensors. The olfactory data describes a set of olfactory patterns for an air sample. The olfactory data is processed to identify attributes of particles in the air sample to generate digital olfactory data. The digital olfactory data comprises metadata describing the attributes of the particles in the air sample to form digital olfactory data. A set of olfactory cohorts is generated using the attributes in the digital olfactory data.

DETAILED DESCRIPTION OF THE INVENTION

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wire line, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Figure 1:
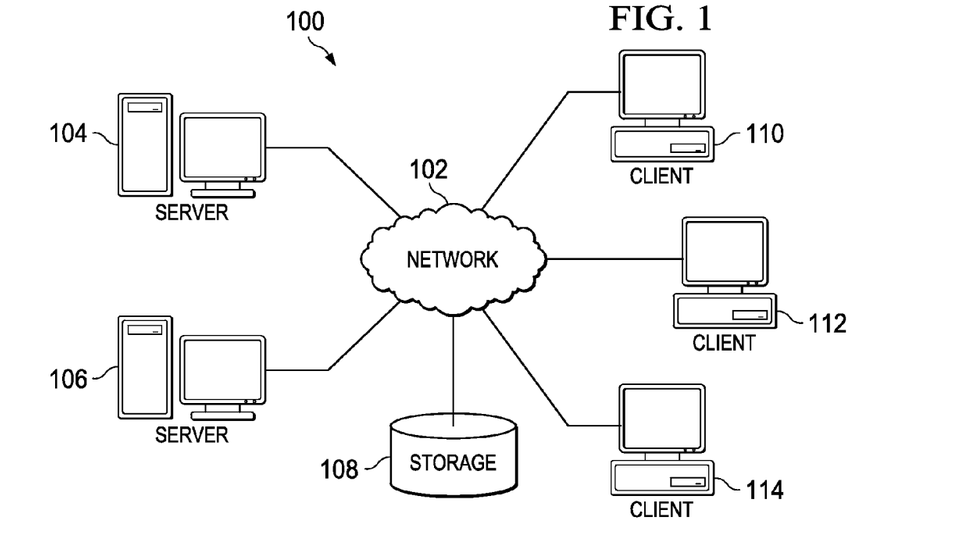
FIG. 1 is a pictorial representation of a network of data processing systems in which illustrative embodiments may be implemented.
Figure 2:
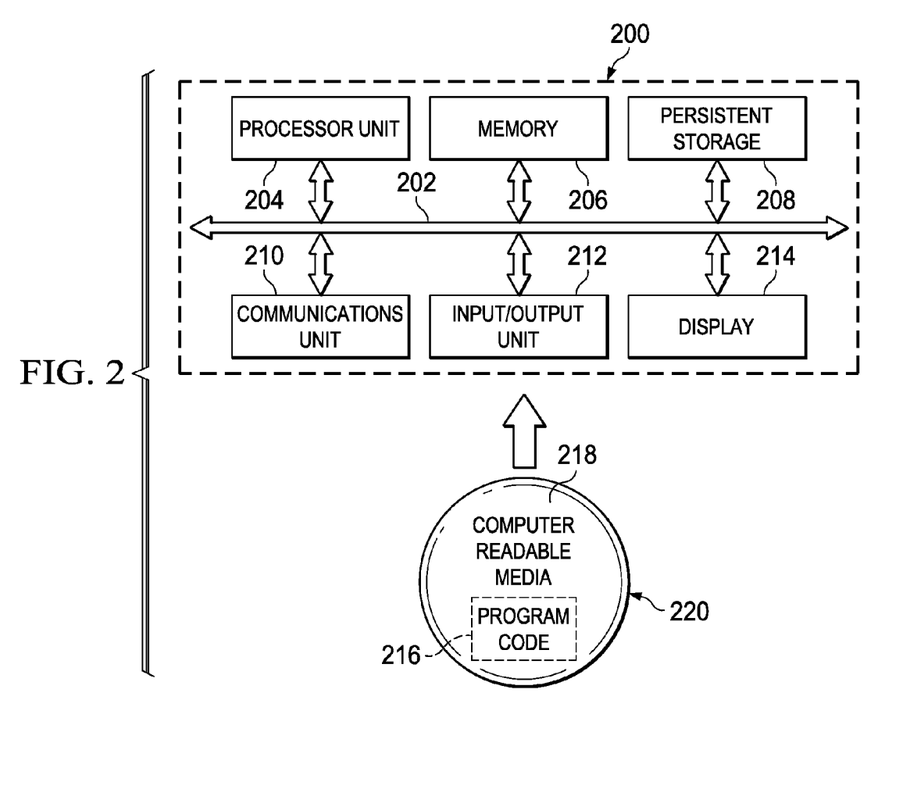
FIG. 2 is a block diagram of a data processing system in which illustrative embodiments may be implemented.

With reference now to the figures and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

Program code located in network data processing system 100 may be stored on a computer recordable storage medium and downloaded to a data processing system or other device for use. For example, program code may be stored on a computer recordable storage medium on server 104 and downloaded to client 110 over network 102 for use on client 110.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

With reference now to FIG. 2, a block diagram of a data processing system is shown in which illustrative embodiments may be implemented. Data processing system 200 is an example of a computer, such as, without limitation, server 104 or client 110 in FIG. 1, in which computer usable program code or instructions implementing the processes may be located for the illustrative embodiments. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices. A storage device is any piece of hardware that is capable of storing information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer recordable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communications links or wireless transmissions containing the program code.

In some illustrative embodiments, program code 216 may be downloaded over a network to persistent storage 208 from another device or data processing system for use within data processing system 200. For instance, program code stored in a computer readable storage medium in a server data processing system may be downloaded over a network from the server to data processing system 200. The data processing system providing program code 216 may be a server computer, a client computer, or some other device capable of storing and transmitting program code 216.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown.

As one example, a storage device in data processing system 200 is any hardware apparatus that may store data. Memory 206, persistent storage 208, and computer readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

A cohort is a group of people, animals, plants, places, or objects that share a common attribute or experience. For example, a group of people born in 1980 may form a birth cohort. A cohort may include one or more sub-cohorts. For example, the birth cohort of people born in 1980 may include a sub-cohort of people born in 1980 in Salt Lake City, Utah. A sub-subcohort may include people born in 1980 in Salt Lake City, Utah to low income, single parent households.

A cohort is generated based on one or more attributes that members of the cohort share in common. The information used to identify the attributes of members of the cohort groups, are typically provided by the members of the cohort groups. However, this information describing attributes and attributes of members of cohort groups may be voluminous, dynamically changing, unavailable, and/or unknown to the member of the cohort group and/or the user selecting members of a cohort group. Moreover, it may be difficult, time consuming, or impractical for an individual to access all the information necessary to accurately generate cohort groups. Moreover, unique cohort groups are typically sub-optimal because individuals lack the skills, time, knowledge, and/or expertise needed to gather cohort attribute information from available sources.

Currently, there are many industries and professions, such as, without limitation, chemistry, research, and medicine, in which it may be desirable to be able to distinguish different aromas and identify sources of particular aromas. Aroma assessment and identification may be performed manually by a human user using natural human olfactory senses to distinguish aromas and identify the sources of different aromas. However, this technique is limited by the range of human ability to "smell" and to distinguish different scents in a multitude of different scents, due to the natural limitations of the relatively weak human olfactory senses.

Dogs typically have a more sensitive sense of smell, and, in some cases, dogs can be trained to identify a particular aroma and the source of an aroma more effectively than a human. For example, cadaver dogs may be used to locate bodies in a disaster area, drug sniffing dogs can be trained to identify the scent of certain illegal drugs, and some dogs have even been trained to smell cancer and other tumors in human patients. However, the illustrative embodiments recognize that the use of dogs is limited by the ability of humans to "communicate" with the animals, the limitations of the canine olfactory ability, and the impracticability of bringing dogs into certain environments.

Electronic sensing technologies have been developed that are capable of reproducing human senses using sensor arrays and pattern recognition algorithms. An electronic nose is an electronic sensing device that detects aromas by using an array of sensors, such as polymer sheets that are capable of conducting electricity. When the array of polymer sheets is exposed to a particular aroma, the polymer sheets expand and the electricity conducing capabilities of the polymer sheets are altered. The information generated by the changing conductivity of the polymer sheets may be used to create olfactory patterns which may be used to identify different aromas.

The illustrative embodiments also recognize that information generated by electronic noses and other chemical sensors are currently only being used to identify odors. The embodiments recognize that the information generated by electronic noses and other chemical sensors identifying odors could be used to identify cohort groups and select members of cohort groups. A cohort group is a group of members that share at least one common attribute. The members of a group may be humans, animals, plants, places, or object. Cohort groups may be used in research, marketing, safety studies, and many other various uses.

Therefore, in one embodiment of the present invention, a computer implemented method, apparatus, and computer program product for generating olfactory cohort data is provided. In other words, the embodiments generate cohort groups and/or select members of cohort groups based on information describing aromas, scents, the chemical composition of airborne substances, and other information describing olfactory attributes.

An olfactory cohort group is a group of members that share one or more attributes associated with olfactory data. The olfactory data in an analog form is received from a set of chemical sensors. As used herein, the term "set" refers to one or more, unless specifically defined differently. Thus, the set of chemical sensors is a set of one or more chemical sensors. A chemical sensor may be implemented as a chemical sensor, a gas identification device, and/or an electronic nose. An electronic nose may also be referred to an artificial nose.

The analog olfactory data describes a set of olfactory patterns for an air sample. The olfactory data is processed to convert the analog olfactory data into a digital format that is compatible with cohort generation engine and to identify attributes of particles in the air sample to generate digital olfactory data. The analog data may be converted into digital olfactory data using any known or available methods.

The digital olfactory data comprises metadata describing the attributes of the olfactory data. An attribute is a characteristic, feature, or other property of a set of airborne aroma producing substances. An aroma includes scent or odor producing particles, such as, without limitation, chemicals, floral substances, gases, odorants, and any other type of aroma producing particles.

Attributes of the olfactory data for an air sample may include, without limitation, a chemical composition of gases and/or compounds in the air sample, a rate of change of the chemical composition of the air sample over time, an origin of gases in the air sample, an identification of gases in the air sample, an identification of odor causing compounds in the air sample, an identification of elements or constituent gases in the air sample, an identification of chemical properties and/or chemical reactivity of elements and/or compounds in the air sample, or any other attributes of particles into the air sample.

An identification of chemical properties may indicate whether a gas or compound in the air sample is toxic, unstable, combustible, and/or reactive with other gases or compounds. For example, if carbon monoxide is a gas that is identified in an air sample, the metadata describing attributes of the particles in the air sample may indicate that a chemical property of carbon monoxide is toxicity to humans. In another example, if a chemical is detected in an air sample, such as sulfur or thiophane, which are commonly used as an odorant in natural gas, the metadata describing the attributes of the air sample may indicate the presence of the odorant and the possibility of the presence of an odorless natural gas which may cause a health and/or safety hazards.

A set of olfactory cohort groups is generated using the attributes described in the metadata in the digital olfactory data. The set of olfactory cohorts may comprise a single cohort group, as well as two or more cohort groups. An olfactory cohort group may have any number of members from a null set to an infinite number of members. In other words, an olfactory cohort group may have no members, a single member, or two or more members that share a common attribute. A member of an olfactory cohort group may include a human, animal, plant, place, location, or object. In one embodiment, the olfactory cohort may be used in a system wide monitoring process to quickly and efficiently pass vital information to a real-time computational process. Thus, the embodiments permit a user to create cohort groups based on olfactory data describing different aromas, sources of different aromas, and other attributes of the aromas in a particular area or environment.

For example, and without limitation, a user may wish to identify every customer in a shopping mall that is wearing perfume or cologne. In such a case, the user may analyze digital olfactory data to identify customers that are a source of recognized perfumes and colognes. These customers may then be selected as members of one or more cohorts of customers using perfume and cologne products. These cohort groups provide an effective tool for users to create cohort groups based on an analysis of olfactory sensory input gathered by a chemical sensor, such as an electronic nose.

Figure 3:
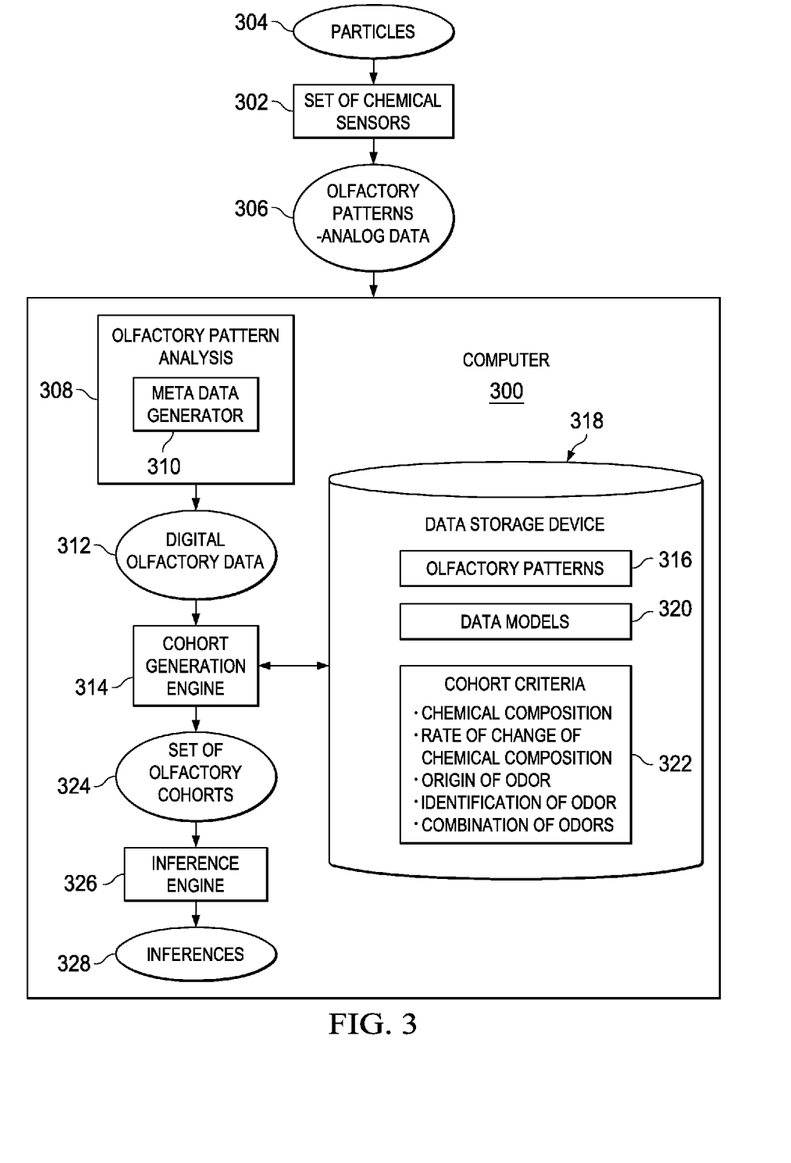
FIG. 3 is a block diagram of an olfactory sensory input analysis system in accordance with an illustrative embodiment.

FIG. 3 is a block diagram of an olfactory sensory input analysis system in accordance with an illustrative embodiment. Computer 300 may be implemented using any type of computing device, such as, but not limited to, a main frame, server, a personal computer, laptop, personal digital assistant (PDA), or any other computing device depicted in FIGS. 1 and 2.

Set of chemical sensors 302 takes an air sample containing particles 304. Set of chemical sensors 302 may include only a single chemical sensor, as well as two or more chemical sensors. A chemical sensor in set of chemical sensors 302 may be implemented as any type of known or available device that can detect airborne chemicals and/or airborne odor causing elements, molecules, gases, compounds, and/or combinations of molecules, elements, gases, and/or compounds in an air sample, such as, without limitation, an airborne chemical sensor, a gas detector, and/or an electronic nose.

In one embodiment, set of chemical sensors 302 is implemented as an array of electronic olfactory sensors and a pattern recognition system that detects and recognizes odors and identifies olfactory patterns associated with different odor causing particles 304. The array of electronic olfactory sensors may include, without limitation, metal oxide semiconductors (MOS), conducting polymers (CP), quartz crystal microbalance, surface acoustic wave (SAW), and field effect transistors (MOSFET).

Particles 304 comprises odor causing particulate matter contained in an air sample captured by set of chemical sensors. Particles 304 may include, without limitation, atoms, molecules, elements, gases, compounds, or any type of airborne odor causing matter. In this embodiment, particles 304 contains odor causing particles. However, particles 304 may also contain odorless substances in addition to the odor causing substances in particles 304.

Set of chemical sensors 302 analyzes particles 304 in the air sample to generate olfactory patterns 306. Olfactory patterns 306 are olfactory data that describe a set of one or more olfactory patterns generated by set of chemical sensors 302. In this example, olfactory patterns 306 are olfactory data in an analog format. However, the olfactory data describing olfactory patterns are not limited to analog data.

An olfactory pattern is a pattern of data that describes changes in one or more olfactory sensors that occur as a result of contact with one or more particles in an air sample. Different olfactory patterns are created as a result of contact with different aroma producing substances. For example, a particular olfactory pattern is produced when an air sample containing sulfur is analyzed by set of chemical sensors 302 and a different olfactory pattern is produced if the air sample contains floral aromas produced by flowers. In other words, a unique olfactory pattern is produced in response to each unique aroma or combination of aromas in an air sample.

Olfactory patterns 306 are used to identify a particular odor and/or combinations of odors in a single air sample or a series of air samples. Olfactory patterns 306 may be generated by set of chemical sensors 302 based on an analysis of particles in a single discrete air sample or based on an analysis of particles in a series of discrete air samples taken at two or more different time intervals.

Set of chemical sensors 302 sends olfactory patterns 306 to olfactory pattern analysis 308 in computer 300. Olfactory pattern analysis 308 converts the analog olfactory patterns 306 generated by set of chemical sensors 302 into a digital format that is compatible with cohort generation engine 314. In other words, olfactory pattern analysis 308 processes olfactory patterns 306 to form digital olfactory data 312. Digital olfactory data 312 identifies attributes of particles 304. Digital olfactory data 312 comprises metadata describing attributes of the particles in the air sample.

Metadata generator 310 is a software component for generating the metadata describing the attributes of the particles. In one non-limiting example, digital olfactory data 312 may be transmitted to cohort generation engine 312 as a digital wave file with the metadata. However, the embodiments are not limited to transmitting digital olfactory data 312 as a digital wave file. Digital olfactory data 312 may be transmitted using any known or available method for transferring or sending data to cohort generation engine 322.

Digital olfactory data 312 comprises metadata describing attributes of the particles in the air sample to form digital olfactory data. Digital olfactory data 312 identifies and describes airborne particles. For example, and without limitation, digital olfactory data 312 may identify toxic airborne chemicals, minute amounts of body products that may be used to identify the presence of humans and/or animals, presence of soap on an employees hands indicating that the employee has washed their hands, the presence of dirt or other contaminants on a restaurant employees hands indicating that the employee needs to wash their hands, whether a person is a smoker, whether someone has smoked in a particular location, identify perfume, after shave, shampoo, conditioner, hand cream, or other product worn by a person, identify a brand of a product used, identify the presence of food stuffs, detect spoilage of foodstuffs, freshness of food stuffs, water, humidity, allergens in the air, such as, without limitation, pet dander, pollen, ragweed, and other allergens.

Digital olfactory data 312 may also be used to identify humans and animals suffering from infections, cancer, tumors, or other aliments. Digital olfactory data 312 may also be used to identify the presence of potentially hazardous substances, such as natural gas, combustible materials, mold, mildew, smoke, asbestos, silica, carbon monoxide, radon gas, tobacco and other carcinogens, and other potentially harmful substances.

Cohort generation engine 314 receives digital olfactory data 312 from olfactory pattern analysis 308. Cohort generation engine 314 may request digital olfactory data 312 from olfactory pattern analysis 308 or from a data storage device where olfactory data is stored. In another embodiment, olfactory pattern analysis 308 automatically sends digital olfactory data 312 to cohort generation engine 314 in real time as digital olfactory data 312 is generated. In yet another embodiment, olfactory pattern analysis 308 sends digital olfactory data 312 to cohort generation engine 314 upon the occurrence of a predetermined event, such as a given time, completion of processing olfactory patterns 306, occurrence of a timeout event, a user request for generation of set of olfactory cohorts 324 based on digital olfactory data 312, or any other predetermined event. Thus, the illustrative embodiments may utilize digital olfactory data 312 in real time as the digital olfactory data is generated or utilize digital olfactory data that is pre-generated or stored in a data storage device until the digital olfactory data is retrieved at some later time.

Cohort generation engine 314 generates set of olfactory cohorts 324 based on digital olfactory data 312. Set of olfactory cohorts 324 is a set of one or more cohort groups that is generated using attributes in digital olfactory data 312. Each cohort group in set of olfactory cohorts 324 may have no members, a single member, or two or more members.

In one embodiment, cohort generation engine 314 compares the olfactory patterns described in digital olfactory data 312 with identified olfactory patterns 316 for comparison. Each different aroma and/or combination of aromas in a particular environment creates a different olfactory pattern. Olfactory patterns 316 are olfactory patterns for known aromas and/or combinations of aromas in a particular environment, such as, without limitation, olfactory patterns associated with known odor causing particles, elements, gases, and/or compounds, known patterns of dispersal, reactivity, and/or changes in composition of known odor causing substances under various conditions and environments. A particular olfactory pattern may be compared to known olfactory patterns. If a match is found, the matching olfactory pattern may be used to identify attributes of the aroma.

Cohort generation engine 314 may optionally process digital olfactory data 312 in data models 320. Data models 320 are a set of one or more data models for processing olfactory data and identifying attributes of particles 304. A data model is a model for structuring, defining, organizing, imposing limitations or constraints, and/or otherwise manipulating data and metadata to produce a result. A data model may be generated using any type of modeling method or simulation including, but not limited to, a statistical method, a data mining method, a causal model, a mathematical model, a marketing model, a behavioral model, a psychological model, a sociological model, or a simulation model.

In one embodiment, digital olfactory data 312 is processed using one or more data models to create one or more olfactory cohorts. For example, a data model may be used to identify customers in a department store that are wearing perfume. This information is used to create a cohort of perfume and/or cologne wearing customers. Another data model may be used to process the same digital olfactory data 312 to create a cohort of customers that are not wearing perfume or cologne.

A cohort may include one or more sub-cohorts. In this example, digital olfactory data 312 may be processed in a data model to identify customers wearing a particular brand of perfume. This information is used to create a sub-cohort of customers wearing the particular brand of perfume. This information may be useful, for example and without limitation, where a store is providing free samples of the particular brand of perfume. The sub-cohort of customers wearing the particular brand of perfume may be used to identify cohorts of customers that tried the free perfume sample, cohorts of customers that declined to try the perfume, and/or cohorts of customers wearing a different brand of perfume than the free sample.

In one embodiment, cohort generation engine 314 generates the cohorts and sub-cohorts in set of olfactory cohorts 324 using cohort criteria 322. In another embodiment, cohort generation engine 314 optionally processes digital olfactory data 312 in data models 320 and uses the results of processing digital olfactory data 312 in data models 320 to generate set of olfactory cohorts 324. In yet another embodiment, cohort generation engine 314 compares of digital olfactory data 312 with known olfactory patterns 316 to generate set of olfactory cohorts 324. In still another embodiment, cohort generation engine 314 uses a combination of cohort criteria 322, data models 320, and/or olfactory patterns 316 to generate set of olfactory cohorts 324. In other words, cohort generation engine 314 may use cohort criteria 322 with olfactory patterns 316 in an absence of data models 320, data models 320 and cohort criteria 322 without olfactory patterns, cohort criteria 322 only, cohort criteria 322, olfactory patterns 316, and data models 320, or any other combination.

Cohort criteria 322 are a set of criteria and/or guidelines for generating set of olfactory cohorts 324. Cohort criteria 322 may include, without limitation, the chemical composition of odor causing particles in the air sample, a rate of change of the chemical composition occurring over time, the origin of the odor causing particles, identification of the odor and/or identification of the source of the odor, identification of a combination of odors, and/or identification of a combination of sources of an odor. The origin of the odor causing particles may be matter in any state, including a solid state, liquid state, semi-solid state, or gaseous state. For example, and without limitation, cohort criteria may specify that a particular cohort group should include all cars that are emitting exhaust from burning fuel with a particular fuel additive.

Set of olfactory cohorts 324 is a set of one or more cohort groups. Each cohort group comprises a set having null to infinity member. An olfactory cohort group may be a null set to an infinite set of members. In other words, an olfactory cohort group may have no members, a single member, or two or more members that share a common attribute. A member of a cohort group may be a human, an animal, a plant, place, thing, or object.

For example, if digital olfactory data 312 indicates the level of sulfur in the air in the vicinity of a volcano is increasing, the digital olfactory data 312 may be used to generate cohorts of active volcanoes that are about to erupt or in the process of erupting. Digital olfactory data 312 may be used to identify cohorts of patients in a hospital with cancer, infections, tumors, diabetes, or other medical conditions. For example, patients with diabetes frequently have a "sweet" smell to their breath. Digital olfactory data 312 may be used to create a cohort of patients having sweet smelling breath and potentially suffering from diabetes. Digital olfactory data 312 may be used to identify employees that have or have not washed their hands with soap. In yet another example, digital olfactory data 312 may be used to identify methane emissions by cows in a particular field or carbon emissions by cars and other vehicles in a given location. Cohorts of high carbon emitting cars and low carbon emitting cars may be generated. The information may also be used to create cohorts of places where carbon emissions are typically higher and cohorts of places in a city where carbon emissions are typically lower.

Thus, the olfactory cohorts may be used for a variety of industrial, medical, health, safety, and research-related endeavors. The olfactory cohorts may be used as a set of methodologies to solve a variety of problems.

In one embodiment, cohort generation engine 314 provides set of olfactory cohorts 324 to inference engine 326. Inference engine 326 is a software component, such as a computer program, that derives inferences from a knowledge base. The knowledge base is a body of facts, criteria, factors, and other information used to generate inference 328. The knowledge base may be stored in one or more local data storage devices on computer 300 and/or stored in one or more remote data storage devices that may be accessed over a network connection. In this example, inference engine 326 derives inferences 328 from set of olfactory cohorts 324 and/or any other data available in the knowledge base. The data in the knowledge base may include data located in a database located locally on computer 300 as well as data located on one or more remote data storage devices that may be accessed using a network connection.

Inferences 328 are conclusions regarding possible future events or future changes in the attributes of cohort groups that are drawn or inferred based on the knowledge base and set of olfactory cohorts 324. For example, and without limitation, set of olfactory cohorts 324 may be analyzed by inference engine 326 to determine whether a particular volcano is about to erupt, an approximate time when the volcano may erupt, and/or a duration of the potential eruption. In another example, inference engine 326 may generate inferences regarding which customers are likely to purchase particular products based on cohorts of customers using those products.

In this embodiment, set of chemical sensors 302 is implemented as a separate device than computer 300. However, in another embodiment, set of chemical sensors 302 and olfactory pattern analysis 308 in computer 300 may be embodied within a single device.

Figure 4:
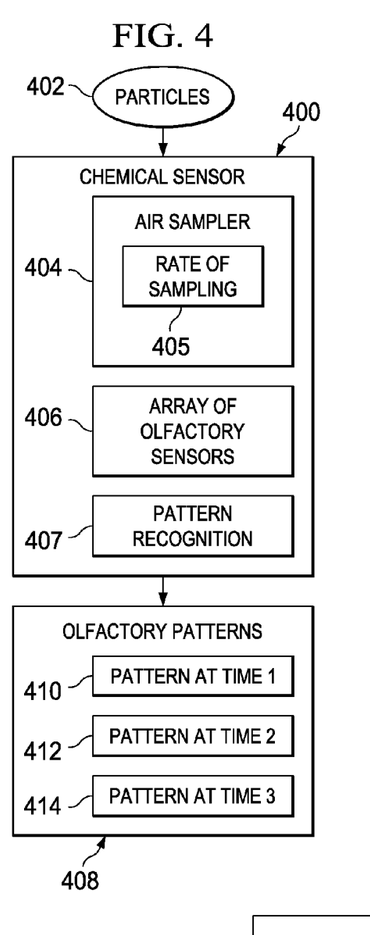
FIG. 4 is a block diagram of a chemical sensor for capturing olfactory sensory input in accordance with an illustrative embodiment.

Turning now to FIG. 4, a block diagram of a chemical sensor for capturing olfactory sensory input is shown in accordance with an illustrative embodiment. Chemical sensor 400 is a device for detecting and/or identifying airborne elements, gases, and/or compounds in particles 402, such as, without limitation, a chemical sensor in set of chemical sensors 302 in FIG. 3. Chemical sensor 400 is an example of one embodiment of a chemical sensor. However, the embodiments disclosed herein are not limited to implementation using chemical sensor 400. These embodiments may be implemented using any type of chemical sensor, such as, without limitation, an electronic nose, a gas identifier, a gas chromatograph, and/or any other type of chemical sensor, or any combination of an artificial nose, a gas identifier, or a gas chromatograph, or other chemical sensor.

Air sampler 404 collects a sample of air at given intervals. Rate of sampling 405 is a software component that controls the rate at which air samples are collected by air sampler 404. Array of olfactory sensors 406 is an array of two or more chemical sensors, such as, but without limitation, a chemical sensor in set of chemical sensors 302 in FIG. 3. Array of olfactory sensors 406 may be implemented as, without limitation, a plurality of metal oxide semiconductors (MOS), conducting polymers (CP), quartz crystal microbalance, surface acoustic wave (SAW), and field effect transistors (MOSFET).

For example, but without limitation, array of olfactory sensors 406 may be implemented as a plurality of polymer films that conduct electricity. When a particle in particles 402 in an air sample comes in contact with one of the polymer films, the electricity conducted through the polymer film is disrupted. Different elements, gases, and compounds disrupt the electricity conducted through the polymer film in different ways. The changes in the conductivity of the polymer films that occurs in the presence of different airborne particles results in different conductivity patterns for different odors. The patterns that result due to the changes in the polymer films and conductivity of the polymer films form olfactory sensory data.

Array of olfactory sensors 406 generates different olfactory sensor data based on the composition of particles 402 in each air sample. Pattern recognition 407 is a pattern recognition algorithm that compares the olfactory sensor data for each air sample with known olfactory patterns to generate analog olfactory patterns 408. Olfactory patterns 408 may include olfactory patterns based on an analysis of a single discrete air sample at pattern at time 1 410 or olfactory patterns based on an analysis of multiple discrete air samples taken at a plurality of different time intervals, such as pattern at time 1 410, pattern at time 2 412, and pattern at time 3 414.

Figure 5:
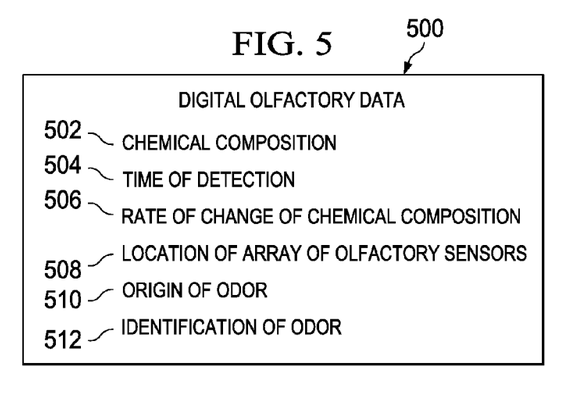
FIG. 5 is a block diagram of digital olfactory data generated based on results of processing captured olfactory sensory input in accordance with an illustrative embodiment.

FIG. 5 is a block diagram of digital olfactory data generated based on results of processing captured olfactory sensory input in accordance with an illustrative embodiment. Digital olfactory data 500 is digital data that includes metadata describing the attributes of particles in a particular air sample or in a series of air samples. Digital olfactory data 500 may describe attributes such as, but without limitation, chemical composition 502 of gases and compounds in an air sample, a time of detection 504 of a particular element, gas, or compound by the set of chemical sensors, the rate of change of chemical composition 506 of a gas or compound occurring over time, the location of the array of olfactory sensors 508 or the location of any other chemical sensor, origin of odor 510 or origin of an odor causing substance, and/or identification of an odor 512 and/or identification of an odor causing substance. However, possible attributes of particles described in digital olfactory data 500 is not limited to attributes 502-512 shown in FIG. 5. Digital olfactory data 500 may include attributes not shown in FIG. 5, such as, without limitation, concentration of a substance in a particular location, rate of dispersal of the substance, or any other possible attributes of airborne substances.

Figure 6:
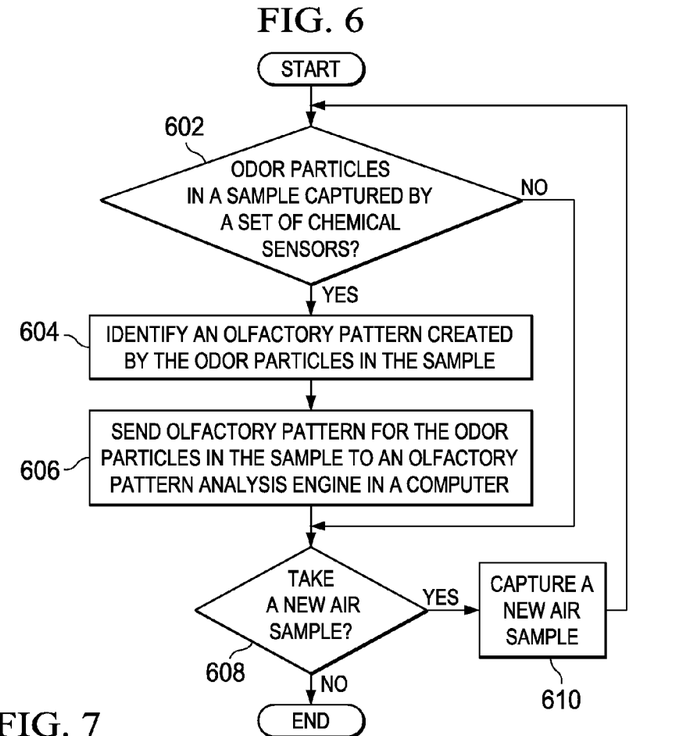
FIG. 6 is a flowchart of a process for capturing olfactory sensory input in accordance with an illustrative embodiment.

Referring now to FIG. 6, a flowchart of a process for capturing olfactory sensory input is depicted in accordance with an illustrative embodiment. The process in FIG. 6 may be implemented by a set of one or more chemical sensors, such as set of chemical sensors 302 in FIG. 3.

The process begins by making a determination as to whether any odor particles are captured in an air sample by the set of chemical sensors (step 602). Odor particles are odor causing particles or particles associated with a resulting odor. Odor particles may be an element, a gas, substance, an odor causing compound, or a combination of elements, gases, and/or compounds. The air sample may contain odorless particles in addition to the odor causing particles. If a given air sample does contain odor particles, the set of chemical sensors identifies an olfactory pattern created by the odor particles in the sample (step 604). The set of chemical sensors sends the olfactory pattern for the odor particles in the air sample to an olfactory pattern analysis engine in a computer (step 606) for analysis, such as, without limitation, computer 300 in FIG. 3.

Returning to step 602, if no odor particles are detected in the air sample or after sending the olfactory pattern for the odor particles in the air sample to the olfactory pattern analysis engine in step 606, a determination is made as to whether to take a new air sample (step 608). If a new air sample is not taken, the process terminates.

Returning to step 608, if a determination is made to take a new air sample, the set of chemical sensors captures a new air sample (step 610). The set of chemical sensors implements steps 602-610 iteratively until no new air samples are taken at step 608 and the process terminates.

Figure 7:
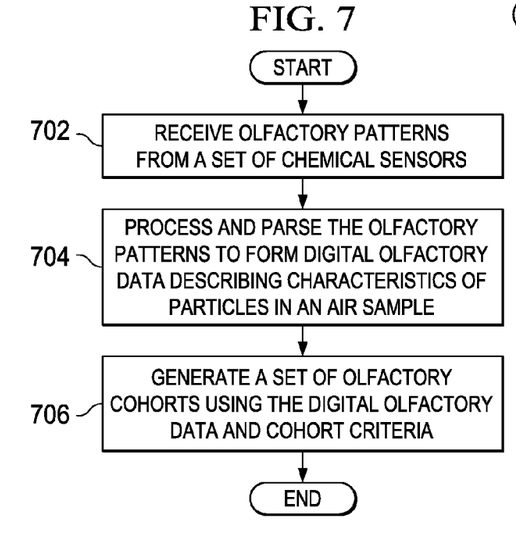
FIG. 7 is a flowchart of a process for generating olfactory cohorts based on olfactory sensory input in accordance with an illustrative embodiment.

Turning now to FIG. 7, a flowchart of a process for generating olfactory cohorts based on olfactory sensory input is shown in accordance with an illustrative embodiment. The process in FIG. 7 may be implemented by software for processing olfactory sensory input, such as olfactory pattern analysis 308 in FIG. 3. Step 706 may be implemented by software for generating olfactory cohorts based on digital olfactory data, such as cohort generation engine 314 in FIG. 3.

The process begins by receiving olfactory patterns for an air sample from a set of chemical sensors (step 702). Olfactory pattern analysis engine processes and parses the olfactory patterns to form digital olfactory data describing attributes of the particles in the air sample (step 704). Any analog data in the olfactory data is converted to a digital format using any known or available method, including, without limitation, gas chromatography. The cohort generation engine generates a set of olfactory cohorts using the digital olfactory data and cohort criteria, such as cohort criteria 322 in FIG. 3 (step 706) with the process terminating thereafter. In another embodiment, the cohort generation engine optionally utilizes data models and/or identified olfactory patterns in addition to cohort criteria or instead of cohort criteria to create the set of olfactory cohorts.

Thus, in one embodiment, a computer implemented method, apparatus, and computer program product for generating olfactory cohort data is provided. Olfactory data is received from a set of chemical sensors. The olfactory data describes a set of olfactory patterns for an air sample. The olfactory data is processed to identify attributes of particles in the air sample to generate digital olfactory data. The digital olfactory data comprises metadata describing identified attributes of the particles in the air sample to form digital olfactory data. In this manner, the olfactory pattern analysis engine converts analog olfactory data into digital data and identifies the chemical composition and other attributes of aromas and substances in the air in a particular area. A set of cohort groups is generated using the digital olfactory data. The cohort groups may be processed by an inference engine to generate inferences regarding future events. Thus, the embodiments may be used to create cohorts based on identified aromas, time of detection of an aroma, origin of an aroma, chemical composition of airborne substances, concentration of aroma causing substances, and/or any other identifiable olfactory attributes.

The digital olfactory data may include attributes of particles such as, without limitation, an identification of molecules, elements, gases, or compounds. The digital olfactory data may be used to identify hazardous substances, radioactivity, identify the presence of humans, plants, and animals, determine whether a person has washed their hands with soap, detect indicators of infection, cancer, or tumors, identify perfumes, aftershave, and scented products used and/or worn by customers in a store, and many other useful attributes of odors and other airborne particles. The olfactory cohorts may be used, for example and without limitation, in sales, marketing, marketing research, medical and diagnostic research, public health, demographic research, marketing trends, safety and/or security. The olfactory cohorts may also be used for quality control in the food industry, in pharmaceuticals, manufacturing, diagnostics, and other areas.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method of generating olfactory cohorts, the computer implemented method comprising:
   receiving olfactory data from a set of chemical sensors, wherein the olfactory data describes a set of olfactory patterns associated with particles in an air sample;
   processing the olfactory data, by an olfactory analysis engine, to identify attributes of the particles in the air sample and generate digital olfactory data, wherein the digital olfactory data comprises metadata describing attributes of the particles in the air sample; and
   generating a set of one or more olfactory cohorts using the attributes in the digital olfactory data, wherein the set of one or more olfactory cohorts are identified by a cohort generation engine analyzing the digital olfactory data in a set of cohort generation data models.

2. The computer implemented method of claim 1, wherein the attributes of the particles in the air sample comprise a concentration of an odor causing substance in the air sample.

3. The computer implemented method of claim 1, wherein the attributes of the particles in the air sample comprise a chemical composition of the particles in the air sample occurring over time.

4. The computer implemented method of claim 1, wherein the attributes of the particles in the air sample comprise a rate of change of a concentration of an odor causing substance in the air sample.

5. The computer implemented method of claim 1, wherein the attributes of the particles in the air sample comprise a rate of change of a chemical composition of the particles in the air sample.

6. The computer implemented method of claim 1, wherein the olfactory data is a first set of olfactory data describing a first set of olfactory patterns for a first air sample taken at a first time interval, and wherein the computer implemented method further comprises:

receiving a second set of olfactory data describing a second set of olfactory patterns for a second air sample taken at a second time interval; and processing the first olfactory data and the second olfactory data to identify the attributes of the particles in the second air sample, wherein the digital olfactory data describing the attributes of the particles in the second air sample is generated based on the first olfactory data and the second olfactory data, and wherein the attributes of the particles in the second air sample comprise a rate of change of chemical composition of the particles over time.

7. The computer implemented method of claim 1, wherein the attributes of the particles in the air sample comprise an identification of an odor and an origin of the odor.

8. The computer implemented method of claim 1, wherein identifying the set of one or more olfactory cohorts using the digital olfactory data further comprises:

analyzing the digital olfactory data using cohort criteria, by a cohort generation engine, to identify the set of one or more olfactory cohorts; and processing the set of one or more olfactory cohorts by an inference engine, wherein the inference engine uses the set of one or more olfactory cohorts to generate a set of inferences.

9. The computer implemented method of claim 1, wherein the particles in the air sample are emitted from persons, and wherein the computer implemented method further comprises:

associating a particular person who emits the particles with a cohort of persons who emit same particles as the particular person.

10. The computer implemented method of claim 1, wherein the set of chemical sensors is an array of olfactory sensors, and wherein an olfactory sensor in the array of olfactory sensors is activated when the olfactory sensor is exposed to a given aroma in a set of aromas.

11. A computer program product for generating olfactory cohorts, the computer program product comprising:

a non-transitory computer readable medium having computer usable program code embodied therewith, the computer usable program code comprising:

computer usable program code configured to receive olfactory data from a set of chemical sensors, wherein the olfactory data describes a set of olfactory patterns associated with particles in an air sample;

computer usable program code configured to process the olfactory data to identify attributes of the particles in the air sample and generate digital olfactory data, wherein the digital olfactory data comprises metadata describing attributes of the particles in the air, sample, and wherein the attributes of the particles in the air sample comprise an identification of an odor and an origin of the odor; and computer usable program code configured to generate a set of one or more olfactory cohort groups using the attributes in the digital olfactory data.

12. The computer implemented method of claim 1, wherein the particles in the air sample are emitted from motor vehicles, and wherein the computer implemented method further comprises:

associating a particular motor vehicle that emits the particles with a cohort of motor vehicles that emit same particles as the particular motor vehicle.

13. The computer program product of claim 11, wherein the attributes of the particles in the air sample comprise a rate of change of a chemical composition of the particles in the air sample occurring over time.

14. The computer program product of claim 11, wherein the attributes of the particles in the air sample comprise a rate of change of a concentration of an odor causing substance in the air sample.

15. The computer program product of claim 11, wherein the attributes of the particles in the air sample comprise a chemical composition of the particles in the air sample.

16. The computer program product of claim 11, wherein the olfactory data is a first set of olfactory data describing a first set of olfactory patterns for a first air sample taken at a first time interval, and further comprising:

computer usable program code configured to receive a second set of olfactory data describing a second set of olfactory patterns for a second air sample taken at a second time interval; and computer usable program code configured to process the first olfactory data and the second olfactory data to identify the attributes of the particles in the second air sample, wherein the digital olfactory data describing the attributes of the particles in the second air sample is generated based on the first olfactory data and the second olfactory data, and wherein the attributes of the particles in the second air sample comprise a rate of change of chemical composition of the particles over time.

17. The computer program product of claim 11, wherein the particles in the air sample are emitted from motor vehicles, and wherein the computer program product further comprises:

computer usable program code configured to associate a particular motor vehicle that emits the particles with a cohort of motor vehicles that emit same particles as the particular motor vehicle.

18. An apparatus comprising:

a bus system;

a communications system coupled to the bus system;

a memory connected to the bus system, wherein the memory includes computer usable program code; and a processing unit coupled to the bus system, wherein the processing unit executes the computer usable program code to:

receive olfactory data from a set of chemical sensors, wherein the olfactory data describes a set of olfactory patterns associated with particles in an air sample, and wherein the olfactory data is a first set of olfactory data describing a first set of olfactory patterns for a first air sample taken at a first time interval;

process the olfactory data to identify attributes of the particles in the air sample and generate digital olfactory data, wherein the digital olfactory data comprises metadata describing attributes of the particles in the air sample;

generate a set of one or more olfactory cohort groups using the digital olfactory data;

receive a second set of olfactory data describing a second set of olfactory patterns for a second air sample taken at a second time interval; and process the first olfactory data and the second olfactory data to identify the attributes of the particles in the second air sample, wherein the digital olfactory data describing the attributes of the particles in the second air sample is generated based on the first olfactory data and the second olfactory data, and wherein the attributes of the particles in the second air sample comprise a rate of change of chemical composition of the particles over time.

19. The apparatus of claim 18, wherein the particles in the air sample are emitted from motor vehicles, and wherein the processing unit further executes computer usable program code to:

associate a particular motor vehicle that emits the particles with a cohort of motor vehicles that emit same particles as the particular motor vehicle.

20. An olfactory cohort generation system comprising:

a set of chemical sensors, wherein the set of chemical sensors generates olfactory data from an air sample;

a data processing system, wherein the data processing system comprises:

an olfactory pattern analysis engine, wherein the olfactory pattern analysis engine:

receives the olfactory data from the set of chemical sensors, wherein the olfactory data describes a set of olfactory patterns associated with particles in an air sample; and processes the olfactory data to identify attributes of the particles in the air sample and generate digital olfactory data, wherein the digital olfactory data comprises metadata describing attributes of the particles in the air sample; and a cohort generation engine, wherein the cohort generation engine generates a set of one or more olfactory cohort groups using the digital olfactory data and cohort criteria wherein the set of one or more olfactory cohort groups are identified by the cohort generation engine analyzing the digital olfactory data in a set of cohort generation data models.

* * * * *

UNITED STATES PATENT AND TRADEMARK OFFICE
Certificate

Patent No. 8,041,516 B2                                                                                            Patented: October 18, 2011

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Robert Lee Angell, Salt Lake City, UT (US); Robert R. Friedlander, Southbury, CT (US); James R. Kraemer, Santa Fe, NM (US); Sergio Borger, Demarest, NJ (US); and Yasodhar Patnaik, Yorktown Heights, NY (US).

Signed and Sealed this Sixteenth Day of April 2013.

ELISEO RAMOS FELICIANO
*Supervisory Patent Examiner*
Art Unit 2857
Technology Center 2800